United States Patent [19]
Donofrio et al.

[11] Patent Number: 5,063,215
[45] Date of Patent: Nov. 5, 1991

[54] BIOCIDAL COMPOSITIONS AND USE THEREOF CONTAINING A SYNERGISTIC MIXTURE OF N-TRIBUTYL TETRADECYL PHOSPHONIUM CHLORIDE AND 3,5-D-THIADIAZINE THIONE

[75] Inventors: Deborah K. Donofrio, The Woodlands; Wilson K. Whitekettle, Conroe, both of Tex.

[73] Assignee: Betz Laboratories, Inc., Trevose, Pa.

[21] Appl. No.: 566,952

[22] Filed: Aug. 13, 1990

[51] Int. Cl.$^5$ .................... A01N 43/86; A01N 43/88; A01N 57/00
[52] U.S. Cl. .................................... 514/75; 162/161; 210/764; 514/223.8
[58] Field of Search ............... 514/75, 223.8; 210/764; 162/161

[56] References Cited

U.S. PATENT DOCUMENTS

| | | | |
|---|---|---|---|
| 3,860,713 | 11/1974 | Shema et al. | 514/223.8 |
| 4,725,587 | 2/1988 | Whitekettle et al. | 514/75 |
| 4,835,143 | 5/1989 | Donofrio et al. | 514/75 |
| 4,835,144 | 5/1989 | Whitekettle et al. | 514/75 |

OTHER PUBLICATIONS

Kelly and Matsen, "In Vitro Activity, Synergism and Testing Parameters of Amikacin, with Comparisons to Other Aminoglycoside Antibiotics", *Antimicrobial Agents and Chemotherapy*, Mar. 1976, pp. 440–447.

Kull, Eisman, Sylwestrowicz and Mayer, "Mixtures of Quaternary Ammonium Compounds and Long-Chain Fatty Acids as Antifungal Agents", *Applied Microbiology*, vol. 9, 1961, pp. 538–541.

*Primary Examiner*—Allen J. Robinson
*Attorney, Agent, or Firm*—Alexander D. Ricci; Richard A. Paikoff

[57] ABSTRACT

A bactericidal composition and method for inhibiting and controlling the growth of the capsulated, facultative bacterium, *Klebsiella pneumoniae*, are disclosed. The composition comprises an amount, effective for the intended purpose of n-tributyl tetradecyl phosphonium chloride (TPC) and 3,5-D-thiadiazine thione. The method comprises administering between about 0.1 to about 200 parts of this combined treatment (based on one million parts of the desired aqueous system) to the particular water containing system for which treatment is desired.

7 Claims, No Drawings

BIOCIDAL COMPOSITIONS AND USE THEREOF CONTAINING A SYNERGISTIC MIXTURE OF N-TRIBUTYL TETRADECYL PHOSPHONIUM CHLORIDE AND 3,5-D-THIADIAZINE THIONE

BACKGROUND OF THE INVENTION

The formation of slimes by microorganisms is a problem that is encountered in many aqueous systems For example, the problem is not only found in natural waters such as lagoons, lakes, ponds, etc., and confined waters as in pools, but also in such industrial systems as cooling water systems, air washer systems and pulp and paper mill systems. All possess conditions which are conducive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms fluorish on the tower proper while other organisms colonize and grow in such areas as the tower sump and the piping and passages of the cooling system. The slime formation not only aids in the deterioration of the tower structure in the case of wooden towers, but also promotes corrosion when it deposits on metal surfaces. Slime carried through the cooling system plugs and fouls lines, valves, strainers, etc., and deposits on heat exchange surfaces. In the latter case, the impedance of heat transfer can greatly reduce the efficiency of the cooling system.

In pulp and paper mill systems, slime formed by microorganisms is commonly encountered and causes fouling, plugging, or corrosion of the system. The slime also becomes entrained in the paper produced to cause breakouts on the paper machines, which results in work stoppages and the loss of production time. The slime is also responsible for unsightly blemishes in the final product, which result in rejects and wasted output.

The previously discussed problems have resulted in the extensive utilization of biocides in cooling water and pulp and paper mill systems. Materials which have enjoyed widespread use in such applications include chlorine, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the tendency of chlorine to react, which results in the expenditure of the chlorine before its full biocidal function is achieved. Other biocides are attended by odor problems and hazards with respect to storage, use or handling which limit their utility. To date, no one compound or type of compound has achieved a clearly established predominance with respect to the applications discussed. Likewise, lagoons, ponds, lakes, and even pools, either used for pleasure purposes or used for industrial purposes for the disposal and storage of industrial wastes, become, during the warm weather, besieged by slime due to microorganism growth and reproduction. In the case of industrial storage or disposal of industrial materials, the microorganisms cause additional problems which must be eliminated prior to the material's use or disposal of the waste.

Naturally, economy is a major consideration with respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides has exhibited a prolonged biocidal effect. Instead, their effectiveness is rapidly reduced as a result of exposure to physical conditions such as temperature, association with ingredients contained by the system toward which they exhibit an affinity or substantivity, etc., with a resultant restriction or elimination of their biocidal effectiveness, or by dilution.

As a consequence, the use of such biocides involves their continuous or frequent addition to systems to be treated and their addition to multiple points or zones in the systems to be treated. Accordingly, the cost of the biocide and the labor cost of applying it are considerable. In other instances, the difficulty of access to the zone in which slime formation is experienced precludes the effective use of a biocide. For example, if in a particular system there is no access to an area at which slime formation occurs the biocide can only be applied at a point which is upstream in the flow system. However, the physical or chemical conditions, e.g., chemical reactivity, thermal degradation, etc., which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at multiple points, and even then a diminishing biocidal effect will be experienced between one point of addition to the system and the next point downstream at which the biocides may be added. In addition to the increased cost of utilizing and maintaining multiple feed points, gross ineconomies with respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

SUMMARY OF THE INVENTION

The biocidal compositions of the present invention comprise, as active ingredients, 1) n-tributyl tetradecyl phosphonium chloride (TPC) and 2) 3,5-D-thiadiazine thione. The full chemical name for 3,5-D-thiadiazine thione is tetrahydro-3,5-dimethyl-2H-1,3,5-thiadiazine-2-thione.

PRIOR ART

TPC is commercially available from Ciba-Geigy under the trademark "Belclene 350" and is marketed as a "broad spectrum biocide specifically developed for the control of microbiological fouling in cooling water systems." Use of the TPC compound in a biological composition is disclosed in U.S. Pat. Nos. 4,725,587 and 4,835,144 (Whitekettle et al.), and U.S. Pat. No. 4,835,143 (Donofrio et al.) of common assignment herewith.

The 3,5-D-thiadiazine thione formulation is commercially available from Akzo under the trademark "N-521".

The synergistic effect obtained by combining TPC and 3,5-D-thiadiazine thione has not been previously disclosed.

DETAILED DESCRIPTION OF THE INVENTION

Surprisingly, the present inventors have found that mixtures of TPC and 3,5-D-thiadiazine thione are especially efficacious in controlling the growth of bacterial microbes, specifically the *Klebsiella pneumoniae* species. This particular species is a member of the capsulated, facultative class of bacteria and is generally present in air, water and soil. These bacteria continually contaminate open cooling systems and pulping and papermaking systems and are among the most common slime formers. The slime may be viewed as being a mass of agglomerated cells stuck together by the cementing action of the gelatinous polysaccharide or proteinaceous secretions around each cell. The slimy mass entraps other debris, restricts water flow and heat transfer, and may serve as a site for corrosion.

The fact that the Klebsiella species used in the tests is a facultative species is important as, by definition, such bacteria may thrive under either aerobic or anaerobic conditions. Accordingly, by reason of demonstrated efficacy in the growth inhibition of this particular species, one can expect similar growth inhibition attributes when other aerobic or anaerobic bacterial species are encountered. It is also expected that these compositions will exhibit similar growth inhibition attributes when fungi and algae species are encountered.

As noted above, TPC is available from Ciba-Geigy and is sold under the trademark "Belclene 350". The physical properties of "Belclene 350" are reported as being:

| | |
|---|---|
| Appearance | Clear, colorless liquid |
| Specific Gravity at 20° C. | 0.96 |
| pH | 7.0–8.0 |
| Boiling Point | 100° C. |
| Freezing Point | −8 to −10° C. |
| Viscosity | 50–80 cP |
| Odor | Slight |
| Solubility Water | Completely miscible in all proportions |
| Methanol | Greater than 50% |
| Isopropanol | Greater than 50% |
| Ethylene Glycol | Greater than 50% |

In accordance with the present invention, the combined TPC and 3,5-D-thiadiazine thione treatment may be added to the desired aqueous system in need of biocidal treatment, in an amount of from about 0.1 to about 200 parts of the combined treatment to one million parts (by weight) of the aqueous medium. Preferably, about 5 to about 50 parts of the combined treatment per one million parts (by weight) of the aqueous medium is added.

The combined treatment is added, for example, to cooling water systems, paper and pulp mill systems, pools, ponds, lagoons, lakes, etc., to control the formation of bacterial microorganisms, which may be contained by, or which may become entrained in, the system to be treated. It has been found that the compositions and methods of utilization of the treatment are efficacious in controlling the facultative bacterium, *Klebsiella pneumoniae*, which may populate these systems. It is thought that the combined treatment composition and method of the present invention will also be efficacious in inhibiting and controlling all types of aerobic and anaerobic bacteria.

Surprisingly, it has been found that when the ingredients are mixed, in certain instances, the resulting mixtures possess a higher degree of bactericidal activity than that of the individual ingredients comprising the mixture. Accordingly, it is possible to produce a highly efficacious bactericide. Because of the enhanced activity of the mixture, the total quantity of the bacterial treatment may be reduced. In addition, the high degree of bactericidal effectiveness which is provided by each of the ingredients may be exploited without use of higher concentrations of each.

The following experimental data were developed. It is to be remembered that the following examples are to be regarded solely as being illustrative, and not as restricting the scope of the invention.

DESCRIPTION OF PREFERRED EMBODIMENT

TPC and 3,5-D-thiadiazine thione were added in varying ratios and over a wide range of concentrations to a liquid nutrient medium which was subsequently inoculated with a standard volume of a suspension of the facultative bacterium *Klebsiella pneumoniae*. Growth was measured by determining the amount of radioactivity accumulated by the cells when 14C-glucose was added as the sole source of carbon in the nutrient medium. The effect of the biocide chemicals, alone and in combination, is to reduce the rate and amount of 14C incorporation into the cells during incubation, as compared to controls not treated with the chemicals. Additions of the biocides, alone and in varying combinations and concentrations, were made according to the accepted "checkerboard" technique described by M. T. Kelley and J. M. Matsen, *Antimicrobial Agents and Chemotherapy*. 9: 440 (1976). Following a two hour incubation, the amount of radioactivity incorporated in the cells was determined by counting (14C liquid scintillation procedures) for all treated and untreated samples. The percent reduction of each treated sample was calculated from the relationship:

$$\frac{\text{Control 14}C \text{ (cpm)} - \text{Treated 14}C \text{ (cpm)}}{\text{Control 14}C \text{ (cpm)}} \times 100 = \% \text{ reduction}$$

Plotting the % reduction of 14C level against the concentration of each biocide acting alone results in a dose-response curve, from which the biocide dose necessary to achieve any given % reduction can be interpolated.

Synergism was determined by the method of calculation described by F. C. Kull, P. C. Eisman, H. D. Sylwestrowicz and R. L. Mayer, *Applied Microbiology* 9,538 (1961) using the relationship:

$$\frac{Q_A}{Q_a} + \frac{Q_B}{Q_b} = \text{synergism index } (SI)$$

where:

$Q_a$ = quantity of compound A, acting alone, producing an end point $Q_b$ = quantity of compound B, acting alone, producing an end point $Q_A$ = quantity of compound A in mixture, producing an end point $Q_B$ = quantity of compound B in mixture, producing an end point The end point used in the calculations is the % reduction caused by each mixture of A and B. $Q_A$ and $Q_B$ are the individual concentrations in the A/B mixture causing a given % reduction. $Q_a$ and $Q_b$ are determined by interpolation from the respective dose-response curves of A and B as those concentrations of A and B acting alone which produce the same % reduction as each specific mixture produced.

Dose-response curves for each active acting alone were determined by linear regression analysis of the dose-response data. Data were fitted to a curve represented by the equation shown with each data set. After linearizing the data, the contributions of each biocide component in the biocide mixtures to the inhibition of radioisotope uptake were determined by interpolation with the dose-response curve of the respective biocide. If, for example, quantities of $Q_A$ plus $Q_B$ are sufficient to give a 50% reduction in 14C content, $Q_a$ and $Q_b$ are those quantities of A or B acting alone, respectively, found to give 50% reduction in 14C content. A synergism index (SI) is calculated for each combination of A and B.

Where the SI is less than 1, synergism exists. Where the SI = 1, additivity exists. Where SI is greater than 1, antagonism exists.

The data in the following tables come from treating *Klebsiella pneumoniae*, a common nuisance bacterial type found in industrial cooling waters and in pulping and paper making systems, with varying ratios and concentrations of TPC and 3,5-D-thiadiazine thione. Shown for each combination is the % reduction of 14C content (% I), the calculated SI, and the weight ratio of TPC and 3,5-D-thiadiazine thione.

TABLE I

| | TPC VS 3,5-D-Thiadiazine Thione | | | |
|---|---|---|---|---|
| ppm TPC[1] | ppm 3,5-D-Thiadiazine Thione[2] | Ratio TPC: 3,5-D-Thiadiazine Thione | % I | SI |
| 0 | 2000 | 0:100 | 84 | |
| 0 | 1500 | 0:100 | 81 | |
| 0 | 1000 | 0:100 | 73 | |
| 0 | 500 | 0:100 | 39 | |
| 0 | 250 | 0:100 | 0 | |
| 0 | 125 | 0:100 | 0 | |
| 100 | 0 | 100:0 | 100 | |
| 80 | 0 | 100:0 | 96 | |
| 50 | 0 | 100:0 | 84 | |
| 40 | 0 | 100:0 | 71 | |
| 25 | 0 | 100:0 | 45 | |
| 20 | 0 | 100:0 | 29 | |
| 100 | 2000 | 1:20 | 98 | 2.08 |
| 100 | 1500 | 1:15 | 98 | 1.87 |
| 100 | 1000 | 1:10 | 98 | 1.67 |
| 100 | 500 | 1:5 | 99 | 1.42 |
| 100 | 250 | 1:2.5 | 99 | 1.32 |
| 100 | 125 | 1:1.25 | 99 | 1.27 |
| 80 | 2000 | 1:25 | 97 | 1.87 |
| 80 | 1500 | 1:18.75 | 97 | 1.65 |
| 80 | 1000 | 1:12.5 | 97 | 1.44 |
| 80 | 500 | 1:6.25 | 97 | 1.23 |
| 80 | 250 | 1:3.125 | 97 | 1.12 |
| 80 | 125 | 1:1.56 | 97 | 1.07 |
| 50 | 2000 | 1:40 | 97 | 1.49 |
| 50 | 1500 | 1:30 | 97 | 1.27 |
| 50 | 1000 | 1:20 | 96 | 1.09 |
| 50 | 500 | 1:10 | 94 | 0.91* |
| 50 | 250 | 1:5 | 92 | 0.84* |

TABLE I-continued

| | TPC VS 3,5-D-Thiadiazine Thione | | | |
|---|---|---|---|---|
| ppm TPC[1] | ppm 3,5-D-Thiadiazine Thione[2] | Ratio TPC: 3,5-D-Thiadiazine Thione | % I | SI |
| 50 | 125 | 1:2.5 | 90 | 0.80* |
| 40 | 2000 | 1:50 | 96 | 1.40 |
| 40 | 1500 | 1:37.5 | 95 | 1.21 |
| 40 | 1000 | 1:25 | 94 | 1.00 |
| 40 | 500 | 1:12.5 | 90 | 0.84* |
| 40 | 250 | 1:6.25 | 86 | 0.79* |
| 40 | 125 | 1:3.125 | 81 | 0.80* |
| 25 | 2000 | 1:80 | 94 | 1.26 |
| 25 | 1500 | 1:60 | 94 | 1.03 |
| 25 | 1000 | 1:40 | 90 | 0.88* |
| 25 | 500 | 1:20 | 80 | 0.80* |
| 25 | 250 | 1:10 | 67 | 0.85* |
| 25 | 125 | 1:5 | 56 | 0.94* |
| 20 | 2000 | 1:100 | 93 | 1.23 |
| 20 | 1500 | 1:75 | 91 | 1.04 |
| 20 | 1000 | 1:50 | 88 | 0.85* |
| 20 | 500 | 1:25 | 73 | 0.83* |
| 20 | 250 | 1:12.5 | 55 | 0.95 |
| 20 | 125 | 1:6.25 | 36 | 1.22 |

[1]product containing 50% actives TPC
[2]product containing 21% actives 3,5-D-thiadiazine thione

TABLE II

| | TPC VS 3,5-D-Thiadiazine Thione | | | |
|---|---|---|---|---|
| ppm TPC[1] | ppm 3,5-D-Thiadiazine Thione[2] | Ratio TPC: 3,5-D-Thiadiazine Thione | % I | SI |
| 0 | 2000 | 0:100 | 77 | |
| 0 | 1500 | 0:100 | 73 | |
| 0 | 1000 | 0:100 | 58 | |
| 0 | 500 | 0:100 | 20 | |
| 0 | 250 | 0:100 | 0 | |
| 0 | 125 | 0:100 | 0 | |
| 100 | 0 | 100:0 | 96 | |
| 80 | 0 | 100:0 | 88 | |
| 50 | 0 | 100:0 | 74 | |
| 40 | 0 | 100:0 | 61 | |
| 25 | 0 | 100:0 | 44 | |
| 20 | 0 | 100:0 | 27 | |
| 100 | 2000 | 1:20 | 95 | 1.80 |
| 100 | 1500 | 1:15 | 95 | 1.63 |
| 100 | 1000 | 1:10 | 97 | 1.39 |
| 100 | 500 | 1:5 | 98 | 1.18 |
| 100 | 250 | 1:2.5 | 98 | 1.10 |
| 100 | 125 | 1:1.25 | 98 | 1.06 |
| 80 | 2000 | 1:25 | 95 | 1.58 |
| 80 | 1500 | 1:18.75 | 95 | 1.41 |
| 80 | 1000 | 1:12.5 | 95 | 1.23 |
| 80 | 500 | 1:6.25 | 94 | 1.08 |
| 80 | 250 | 1:2.5 | 93 | 1.01 |
| 80 | 125 | 1:1.25 | 94 | 0.94* |
| 50 | 2000 | 1:40 | 93 | 1.31 |
| 50 | 1500 | 1:30 | 94 | 1.10 |
| 50 | 1000 | 1:20 | 87 | 1.10 |
| 50 | 500 | 1:10 | 86 | 0.90* |
| 50 | 250 | 1:5 | 81 | 0.89* |
| 50 | 125 | 1:2.5 | 78 | 0.89* |
| 40 | 2000 | 1:50 | 91 | 1.26 |
| 40 | 1500 | 1:37.5 | 90 | 1.09 |
| 40 | 1000 | 1:25 | 88 | 0.94* |
| 40 | 500 | 1:12.5 | 80 | 0.88* |
| 40 | 250 | 1:6.25 | 71 | 0.93* |
| 40 | 125 | 1:3.13 | 67 | 0.94* |
| 25 | 2000 | 1:80 | 89 | 1.13 |
| 25 | 1500 | 1:60 | 87 | 0.98 |
| 25 | 1000 | 1:40 | 83 | 0.84* |
| 25 | 500 | 1:20 | 70 | 0.83* |
| 25 | 250 | 1:10 | 58 | 0.88* |
| 25 | 125 | 1:5 | 51 | 0.91* |
| 20 | 2000 | 1:100 | 86 | 1.15 |
| 20 | 1500 | 1:75 | 84 | 0.98 |
| 20 | 1000 | 1:50 | 79 | 0.85* |
| 20 | 500 | 1:25 | 62 | 0.88* |
| 20 | 250 | 1:12.5 | 44 | 1.05 |

TABLE II-continued

| ppm TPC[1] | TPC VS 3,5-D-Thiadiazine Thione | | | |
|---|---|---|---|---|
| | ppm 3,5-D-Thiadiazine Thione[2] | Ratio TPC: 3,5-D-Thiadiazine Thione | % I | SI |
| 20 | 125 | 1:6.25 | 35 | 1.05 |

[1] product containing 50% actives TPC
[2] product containing 21% actives 3,5-D-thiadiazine thione Asterisks in the SI column indicate synergistic combinations in accordance with the Kull method supra.

In Tables I and II, differences seen between the replicates are due to normal experimental variance.

In accordance with Tables I-II supra., unexpected results occurred more frequently within the product ratios of "Belclene 350" to 3,5-D-thiadiazine thione of from about 1:2.5 to 1:50. Since the "Belclene 350" product contains about 50% active biocidal component (i.e., tri n-butyl tetradecyl phosphonium chloride) and the 3,5-D-thiadiazine thione product contains about 21% active biocidal component, when based on the active biocidal component, unexpected results appear more frequently within the range of active component of "Belclene 350": 3,5-D-thiadiazine thione of about 1:1 to 1:21. At present, it is most preferred that any commercial product embodying the invention comprises a weight ratio of active component of about 1:2 TPC : 3,5-D-thiadiazine thione.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A bacterial inhibiting composition comprising a synergistic mixture of (a) n-tributyl tetradecyl phosphonium chloride (TPC) and (b) 3,5-D-thiadiazine thione wherein the weight ratio of (a):(b) is from about 1:1 to 1:21.

2. The composition as recited in claim 1 wherein the weight ratio of (a) to (b) is about 1:2.

3. A method for controlling the growth of *Klebsiella pneumoniae* bacteria in an aqueous system which comprises adding to said system from about 0.1 to 200 parts per weight of a composition per one million parts per weight of said aqueous system, said composition comprising a synergistic mixture of (a) n-tributyl tetradecyl phosphonium chloride (TPC) and (b) 3,5-D-thiadiazine thione, the weight ratio of (a):(b) being from about 1:1 to 1:21.

4. The method as recited in claim 3 wherein the weight ratio of (a):(b) is about 1:2.

5. The method as recited in claim 3 wherein said composition is added to said system in an amount of from about 5 to about 50 parts per million of said aqueous system.

6. The method as recited in claim 3 wherein said aqueous system comprises a cooling water system.

7. The method as recited in claim 3 wherein said aqueous system comprises a pulping and papermaking system.

* * * * *